US007612017B2

(12) United States Patent
Feucht et al.

(10) Patent No.: US 7,612,017 B2
(45) Date of Patent: Nov. 3, 2009

(54) SELECTIVE HERBICIDES BASED ON SUBSTITUTED AMINOTRIAZINONES AND SUBSTITUTED BENZOYLCYCLOHEXANEDIONES

(75) Inventors: Dieter Feucht, Eschborn (DE); Peter Dahmen, Neuss (DE); Joachim Meyer, Leverkusen (DE); Olivier Fanica, Montigny-sur-Loing (FR)

(73) Assignee: Bayer CropScience AG, Monheim (DE)

( * ) Notice: Subject to any disclaimer, the term of this patent is extended or adjusted under 35 U.S.C. 154(b) by 597 days.

(21) Appl. No.: 10/508,503

(22) PCT Filed: Mar. 10, 2003

(86) PCT No.: PCT/EP03/02416

§ 371 (c)(1),
(2), (4) Date: Feb. 10, 2005

(87) PCT Pub. No.: WO03/079789

PCT Pub. Date: Oct. 2, 2003

(65) Prior Publication Data

US 2005/0143261 A1     Jun. 30, 2005

(30) Foreign Application Priority Data

Mar. 22, 2002   (DE)   ................... 102 12 887

(51) Int. Cl.
*A01N 43/64* (2006.01)
(52) U.S. Cl. ...................................... 504/133
(58) Field of Classification Search .............. 504/116.1, 504/133
See application file for complete search history.

(56) References Cited

U.S. PATENT DOCUMENTS

| | | | |
|---|---|---|---|
| 3,671,523 A | 6/1972 | Westphal et al. | 260/248 AS |
| 3,910,909 A | 10/1975 | Draber et al. | 260/248 AS |
| 3,961,936 A | 6/1976 | Westphal et al. | 71/93 |
| 3,966,715 A | 6/1976 | Westphal et al. | 260/240 A |
| 4,036,632 A | 7/1977 | Westphal et al. | 71/93 |
| 4,346,220 A * | 8/1982 | Fawzi | 544/182 |
| 4,780,127 A * | 10/1988 | Michaely et al. | 504/348 |
| 4,946,981 A | 8/1990 | Carter et al. | 558/415 |
| 5,006,162 A | 4/1991 | Carter | 71/123 |
| 5,173,104 A * | 12/1992 | Feucht | 504/133 |
| 5,506,195 A | 4/1996 | Ensminger et al. | 504/350 |
| 5,545,607 A * | 8/1996 | Quaghebeur et al. | 504/130 |
| 6,511,940 B1 | 1/2003 | Ziemer et al. | 504/118 |
| 2003/0171220 A1 | 9/2003 | Ziemer et al. | 504/271 |

FOREIGN PATENT DOCUMENTS

| | | |
|---|---|---|
| WO | 02/21920 | 3/2002 |
| WO | 02/100173 | 12/2002 |
| WO | 03/005820 | 1/2003 |
| WO | 03/028450 | 4/2003 |
| WO | WO 03028450 A2 * | 4/2003 |

OTHER PUBLICATIONS

Davies, J., Review Herbicide Safeners: a Review, Society of Chemical Industry, 1999, Pesticide Science 55: 1043-1058.*
Walton, J., Specific Binding of a Dichloroacetamide Herbicide Safener in Maize at a Site That Also Binds Thiocarbamate and Chloroacetanilide Herbicides, University of California, 1995, Plant Physiology 109:213-219.*
Rouchaud, J., Soil Dissipation of the Post-Emergence Herbicide Sulcotrione in Maize Crops Treated with Organic Fertilizers, Springer-Verlag, 1996, 57:398-405.*
Weeds, 15, (month unavailable) 1967, pp. 20-22, S.R. Colby, "Calculating Synergistic and Antagonistic Responses of Herbicide Combinations".

* cited by examiner

*Primary Examiner*—Johann R Richter
*Assistant Examiner*—Danielle Sullivan
(74) *Attorney, Agent, or Firm*—Richard E. L. Henderson

(57) ABSTRACT

The invention relates to novel herbicidal, synergistic active compound combinations comprising (a) substituted aminotriazinones and (b) substituted benzoylcyclohexanediones and, if appropriate, additionally (c) a compound which improves crop plant compatibility, and which can be used with particularly good results for the selective control of weeds in various crops of useful plants.

4 Claims, No Drawings

SELECTIVE HERBICIDES BASED ON SUBSTITUTED AMINOTRIAZINONES AND SUBSTITUTED BENZOYLCYCLOHEXANEDIONES

The present patent application has been filed under 35 U.S.C. 371 as a national stage application of PCT/EP03/02416, filed Mar. 10, 2003, which was published in German as International Patent Publication WO 03/079789 on Oct. 2, 2003, which is entitled to the right of priority of German Patent Application 102 12 887.1, filed Mar. 22, 2002.

The invention relates to novel herbicidal, synergistic active compound combinations comprising firstly known substituted aminotriazinones and secondly known substituted benzoylcyclohexanediones and, if appropriate, additionally a compound which improves crop plant compatibility, and which can be used with particularly good results for the selective control of weeds in various crops of useful plants.

Certain substituted aminotriazinones, such as, for example, the compounds 4-amino-6-(1,1-dimethylethyl)-3-methylthio-1,2,4-triazin-5(4H)-one (metribuzin), 4-amino-3-methyl-6-phenyl-1,2,4-triazin-5(4H)-one (metamitron) and 4-amino-6-(1,1-di-methylethyl)-3-ethylthio-1,2,4-triazin-5(4H)-one (ethiozin), are known as herbicidally active substances (cf. DE-1795784, DE-2138031, U.S. Pat. No. 4,036,632).

Certain substituted benzoylcyclohexanediones, such as, for example, the compounds 2-(2-chloro-4-methylsulphonyl-benzoyl)-1,3-cyclohexanedione (sulcotrione) and 2-(4-methylsulphonyl-2-nitrobenzoyl)-1,3-cyclohexanedione (mesotrione), are likewise known as herbicidally active substances (cf. EP-0137963 and WO-96/13163).

Surprisingly, it has now been found that a number of known active compounds from the group of the substituted aminotriazinones, when used together with known herbicidally active compounds from the group of the substituted benzoylcyclohexanediones, exhibit synergistic effects with respect to the action against weeds and can be used particularly advantageously as broad-spectrum combination preparations for the selective control of weeds in crops of useful plants, such as, for example, in cotton, barley, potatoes, maize, oilseed rape, rice, rye, soya beans, sunflowers, wheat, sugar cane and sugar beet.

The invention provides selectively herbicidal compositions, characterized in that they comprise an effective amount of an active compound combination comprising (a) at least one substituted aminotriazinone of the general formula (I)

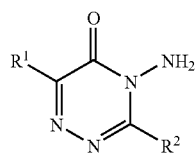

(I)

in which $R^1$ represents straight-chain or branched alkyl having 1 to 6 carbon atoms or represents phenyl and $R^2$ represents in each case straight-chain or branched alkyl or alkylthio having in each case 1 to 6 carbon atoms ("compounds of group 1") and (b) at least one substituted benzoylcyclohexanedione of the general formula (II)

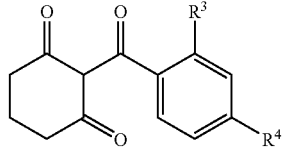

(II)

in which $R^3$ represents nitro, cyano, halogen, or represents in each case halogen-substituted, in each case straight-chain or branched alkyl, alkoxy, alkylthio, alkylsulphinyl or alkylsulphonyl having in each case 1 to 6 carbon atoms, and $R^1$ represents nitro, cyano, halogen, represents in each case optionally halogen-, $C_1$-$C_4$-alkoxy-, $C_1$-$C_4$-alkylthio-, $C_1$-$C_4$-alkylsulphinyl- or $C_1$-$C_4$-alkyl-sulphonyl-substituted, in each case straight-chain or branched alkyl, alkoxy, alkylthio, alkylsulphinyl or alkylsulphonyl having in each case 1 to 6 carbon atoms, or represents alkylamino, dialkylamino, dialkylaminocarbonyl or dialkylaminosulphonyl having in each case 1 to 6 carbon atoms in the alkyl groups which are in each case straight-chain or branched ("active compounds of group 2")

and also, if appropriate, additionally (c) a compound which improves crop plant compatibility, from the following group of compounds:

4-dichloroacetyl-1-oxa-4-azaspiro[4.5]decane (AD-67), 1-dichloroacetylhexahydro-3,3,8a-trimethylpyrrolo[1,2-a] pyrimidin-6(2H)-one (BAS-145138), 4-dichloroacetyl-3,4-dihydro-3-methyl-2H-1,4-benzoxazine (benoxacor), 1-methylhexyl 5-chloro-quinoxalin-8-oxyacetate (cloquintocet-mexyl), α-(cyanomethoximino)phenyl-acetonitrile (cyometrinil), 2,4-dichlorophenoxyacetic acid (2,4-D), 2,2-dichloro-N-(2-oxo-2-(2-propenylamino)ethyl)-N-(2-propenyl)acetamide (DKA-24), 2,2-dichloro-N,N-di-2-propenylacetamide (dichlomid), N-(4-methylphenyl)-N'-(1-methyl-1-phenylethyl)urea (daimuron, dymron), 4,6-dichloro-2-phenylpyrimidine (fenclorim), ethyl 1-(2,4-dichlorophenyl)-5-trichloromethyl-1H-1,2,4-triazole-3-carboxylate (fenchlorazol-ethyl), phenylmethyl 2-chloro-4-trifluoromethylthiazole-5-carboxylate (flurazole), 4-chloro-N-(1,3-dioxolan-2-ylmethoxy)-α-trifluoroacetoxyphenoxime (flux-ofenim), 3-dichloroacetyl-5-(2-furanyl)-2,2-dimethyloxazolidine (furilazole, MON-13900), ethyl 4,5-dihydro-5,5-diphenyl-3-isoxazolecarboxylate (isoxadifen-ethyl), (4-chloro-2-methylphenoxy)acetic acid (MCPA), (+/−)-2-(4-chloro-2-methylphenoxy)propanoic acid (mecoprop), diethyl 1-(2,4-dichlorophenyl)-4,5-dihydro-5-methyl-1H-pyrazole-3,5-dicarboxylate (mefenpyr-diethyl), 2-dichloromethyl-2-methyl-1,3-dioxolane (MG-191), 1,8-naphthalic anhydride, α-(1,3-dioxolan-2-ylmethoximino) phenylacetonitrile (oxabetrinil), 2,2-dichloro-N-(1,3-dioxolan-2-ylmethyl)-N-(2-propenyl)acetamide (PPG-1292), 3-dichloroacetyl-2,2,5-trimethyloxazolidine (R-29148), N-cyclopropyl-4-[[(2-methoxy-5-methylbenzoyl)amino] sulphonyl]benzamide, N-[[(4-methoxyacetylamino)phenyl] sulphonyl]-2-methoxybenzamide and N-[[(4-methylaminocarbonylamino)phenyl]sulphonyl]-2-methoxybenzamide (the latter are in each case known from WO-A-99/66795)

("active compounds of group 3").

In general, 0.01 to 100 parts by weight of an active compound of group 2 are present per part by weight of an active compound of group 1.

Preferred meanings of the groups listed above in connection with the formula (I) are defined below.

$R^1$ preferably represents straight-chain or branched alkyl having 1 to 5 carbon atoms or represents phenyl.

$R^2$ preferably represents in each case straight-chain or branched alkyl or alkylthio having in each case 1 to 5 carbon atoms.

$R^1$ particularly preferably represents methyl, ethyl, n- or i-propyl, n-, i-, s- or t-butyl, or represents phenyl.

$R^2$ particularly preferably represents methyl, ethyl, n- or i-propyl, n-, i-, s- or t-butyl, methylthio, ethylthio, n- or i-propylthio, n-, i-, s- or t-butylthio.

$R^1$ very particularly preferably represents n- or i-propyl, n-, i-, s- or t-butyl, or represents phenyl.

$R^2$ very particularly preferably represents methyl, ethyl, n- or i-propyl, methyl-thio, ethylthio, n- or i-propylthio.

Very particularly preferred mixing components of the general formula (I) which may be mentioned by way of example are:

4-amino-6-(1,1-dimethylethyl)-3-methylthio-1,2,4-triazin-5 (4H)-one (metribuzin), 4-amino-3-methyl-6-phenyl-1,2,4-triazin-5(4H)-one (metamitron) and 4-amino-6-(1,1-dimethylethyl)-3-ethylthio-1,2,4-triazin-5(4H)-one (ethiozin).

Very particular emphasis is given to the compound 4-amino-6-(1,1-dimethylethyl)-3-methylthio-1,2,4-triazin-5 (4H)-one (metribuzin).

Preferred meanings of the groups listed above in connection with the formula (II) are defined below.

$R^3$ preferably represents nitro, cyano, halogen, or represents in each case optionally halogen-substituted, in each case straight-chain or branched alkyl, alkoxy, alkylthio, alkylsulphinyl or alkylsulphonyl having in each case 1 to 5 carbon atoms.

$R^4$ particularly preferably represents nitro, cyano, halogen, represents in each case optionally halogen-, $C_1$-$C_4$-alkoxy-, $C_1$-$C_4$-alkylthio-, $C_1$-$C_4$-alkyl-sulphinyl- or $C_1$-$C_4$-alkylsulphonyl-substituted, in each case straight-chain or branched alkyl, alkoxy, alkylthio, alkylsulphinyl or alkylsulphonyl having in each case 1 to 5 carbon atoms, or represents alkylamino, dialkylamino, dialkylaminocarbonyl or dialkylaminosulphonyl having in each case 1 to 5 carbon atoms in the alkyl groups, which are in each case straight-chain or branched.

$R^3$ particularly preferably represents nitro, cyano, fluorine, chlorine, bromine, iodine, or represents in each case optionally fluorine- and/or chlorine-substituted methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, n- or i-propylsulphinyl, methylsulphonyl or ethylsulphonyl.

$R^4$ particularly preferably represents nitro, cyano, fluorine, chlorine, bromine, iodine, represents in each case optionally fluorine-, chlorine-, methoxy-, ethoxy-, n- or i-propoxy-, methylthio-, ethylthio-, n- or i-propylthio-, methylsulphinyl-, ethylsulphinyl-, n- or i-propylsulphinyl-, methylsulphonyl- or ethylsulphonyl-substituted methyl-, ethyl-, n- or i-propyl, n-, i-, s- or t-butyl, methoxy, ethoxy, n- or i-propoxy, methylthio, ethylthio, n- or i-propylthio, methylsulphinyl, ethylsulphinyl, n- or i-propylsulphinyl, methylsulphonyl or ethylsulphonyl, or represents methylamino, ethylamino, n- or i-propylamino, dimethylamino, diethylamino, dipropylamino, dimethylaminocarbonyl, diethylaminocarbonyl, dimethylaminosulphonyl or diethylaminosulphonyl.

$R^3$ very particularly preferably represents nitro, cyano, fluorine, chlorine, bromine, or represents in each case optionally fluorine- and/or chlorine-substituted methyl, ethyl, methoxy, ethoxy, methylthio, ethylthio, methyl-sulphinyl, ethylsulphinyl, methylsulphonyl or ethylsulphonyl.

$R^4$ very particularly preferably represents nitro, cyano, fluorine, chlorine, bromine, or represents in each case optionally fluorine-, chlorine-, methoxy-, ethoxy-, methylthio-, ethylthio-, methylsulphinyl-, ethylsulphinyl-, methylsulphonyl-, or ethylsulphonyl-substituted methyl, ethyl, methoxy, ethoxy, methylthio, ethylthio, methylsulphinyl, ethylsulphinyl, methylsulphonyl or ethylsulphonyl.

Very particularly preferred mixing components of the general formula (II) which may be mentioned by way of example are:

2-(2-chloro-4-methylsulphonylbenzoyl)-1,3-cyclohexanedione (sulcotrione) and 2-(4-methylsulphonyl-2-nitrobenzoyl)-1,3-cyclohexanedione (mesotrione).

Very particular emphasis is given to the compound 2-(2-chloro-4-methyl-sulphonylbenzoyl)-1,3-cyclohexanedione (sulcotrione).

The compositions according to the invention preferably contain one active compound of group 1 and one active compound of group 2 and, if appropriate, additionally also one active compound of group 3.

Very particular preference is given to combinations of the active compounds 4-amino-6-(1,1-dimethylethyl)-3-methylthio-1,2,4-triazin-5(4H)-one (metribuzin) and 2-(2-chloro-4-methylsulphonylbenzoyl)-1,3-cyclohexanedione (sulcotrione).

Surprisingly, it has now been found that the above-defined active compound combinations of the substituted aminotriazinones of the formula (I) and the substituted benzoylcyclohexanediones of the formula (II) and, if appropriate, additionally a compound which improves crop-plant compatibility exhibit a particularly high herbicidal activity combined with very good crop plant compatibility and can be used for the selective control of monocotyledonous and dicotyledonous weeds in a variety of crops, especially in cotton, barley, potatoes, maize, oilseed rape, rice, rye, soya beans, sunflowers, wheat, and sugar cane and sugar beet, in particular in barley, maize, rice and wheat, very particularly in maize.

Surprisingly, the herbicidal activity of the active compound combinations according to the invention of compounds of the abovementioned groups 1 and 2 exceeds the total of the actions of the individual active compounds considerably.

Thus, not just a complementation of actions but a synergistic effect is present which could not have been predicted. The novel active compound combinations are well tolerated in a variety of crops, also effecting good control of weeds which are otherwise difficult to control. Thus, the novel active compound combinations are a valuable addition to the herbicides.

The synergistic effect of the active compound combinations according to the invention is particularly strongly pronounced in certain concentration ratios. However, the weight ratios of the active compounds in the active compound combinations may be varied within relatively wide ranges. In general, from 0.01 to 100 parts by weight, preferably from 0.02 to 50 parts by weight and particularly preferably from 0.05 to 10 parts by weight of active compound of group 2 are used per part by weight of active compound of the formula (I).

The following may be particularly emphasized as mixing components from amongst the active compounds of group 3:

1-methyl-hexyl 5-chloroquinoline-8-oxyacetate (cloquintocet-mexyl), ethyl 4,5-di-hydro-5,5-diphenyl-3-isoxazolecarboxylate (isoxadifen-ethyl) and diethyl 1-(2,4-di-chlorophenyl)-4,5-dihydro-5-methyl-1H-pyrazole-3,5-dicarboxylate (mefenpyr-diethyl) particularly suitable for improving tolerance in barley and wheat and to a certain extent also in maize and rice, and 4-dichloroacetyl-1-oxa-4-azaspiro[4.5]-decane (AD-67), 1-dichloroacetyl-hexahydro-3,3,8a-trimethylpyrrolo[1,2-a]-pyrimidin-6(2H)-one (BAS-145138), 4-dichloroacetyl-3,4-dihydro-3-methyl-2H-1,4-benzoxazin (benoxacor), 2,2-dichloro-N,N-di-2-propenylacetamide (dichlormid), 3-dichloroacetyl-5-(2-furanyl)-2,2-dimethyloxazolidine (flurilazole, MON-13900), and 3-dichloroacetyl-2,2,5-trimethyloxazolidine (R-29148) particularly suitable for improving tolerance in maize.

All plants and plant parts can be treated in accordance with the invention. Plants are to be understood as meaning in the present context all plants and plant populations such as desired and undesired wild plants or crop plants (inclusive of naturally occurring crop plants). Crop plants can be plants which can be obtained by conventional plant breeding and optimization methods or by biotechnological and recombinant methods or by combinations of these methods, inclusive of the transgenic plants and inclusive of the plant varieties protectable or not protectable by plant breeders' rights. Plant parts are to be understood as meaning all aerial and subterranean plant parts and organs of the plants such as shoot, leaf, flower and root, examples which may be mentioned being leaves, needles, stalks, trunks, flowers, fruiting bodies, fruits, and seeds, and also roots, tubers and rhizomes. The plant parts also include vegetative and generative propagation material, for example cuttings, tubers, rhizomes, seedlings and seeds.

As already mentioned above, it is possible to treat all plants and their parts according to the invention. In a preferred embodiment, wild plant species and plant cultivars, or those obtained by conventional biological breeding, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof are treated. The term "parts" or "parts of plants" or "plant parts" has been explained above.

Particularly preferably, plants of the plant cultivars which are in each case commercially available or in use are treated according to the invention. By plant cultivars are meant plants having new properties ("traits"), bred either by conventional breeding, by mutagenesis or by recombinant DNA techniques. They may be cultivars, biotypes and genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions to be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which are actually to be expected.

The preferred transgenic plants or plant cultivars (i.e. those obtained by genetic engineering) which are to be treated according to the invention include all plants which, in the genetic modification, received genetic material which imparted particularly advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, oilseed rape and also fruit plants (with the fruits apples, pears, citrus fruits and grapevines), and particular emphasis is given to maize, soya beans, potatoes, cotton and oilseed rape. Traits that are emphasized are in particular increased defence of the plants against insects by toxins formed in the plants, in particular those formed by the genetic material from Bacillus thuringiensis (for example by the genes CryIA(a), CryIA(b), CryIA(c), CryIIA, CryIIIA, CryIIIB2, Cry9c, Cry2Ab, Cry3Bb and CryIF and also combinations thereof) (hereinbelow referred to as "Bt plants"). Traits that are also particularly emphasized are the increased defence of plants against fungi, bacteria and viruses by Systematic Acquired Resistance (SAR), systemine, phytoalexins, elicitors and resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these or still to be developed genetic traits, which plants will be developed and/or marketed in the future.

The plants listed can be treated according to the invention in a particularly advantageous manner with the compounds of the general formula I or the active compound mixtures according to the invention. The preferred ranges stated above for the active compounds or mixtures also apply to the treatment of these plants. Particular emphasis is given to the treatment of plants with the compounds or the mixtures specifically mentioned in the present text.

The treatment according to the invention of the plants and plant parts with the active compounds is carried out directly or by allowing the compounds to act on their surroundings, environment or storage space by the customary treatment methods, for example by immersion, spraying, evaporation, fogging, scattering, painting on and, in the case of propagation material, in particular in the case of seeds, also by applying one or more coats.

Amongst the plants obtained by biotechnological and recombinant methods, or by combining these methods, plants which are emphasized are those which tolerate so-called ALS, 4-HPPD, EPSP and/or PPO inhibitors, such as, for example, Acuron plants.

The active compounds according to the invention can be used, for example, in the following plants:

Dicotyledonous weeds of the genera: *Abutilon, Amaranthus, Ambrosia, Anoda, Anthemis, Aphanes, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindemia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

Dicotyledonous crops of the genera: *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia.*

Monocotyledonous weeds of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Monocotyledonous crops of the genera: *Allium, Ananas, Asparagus, Avena, Hordeum, Oryza, Panicum, Saccharum, Secale, Sorghum, Triticale, Triticum, Zea.*

However, the use of the active compound combinations according to the invention is in no way restricted to these genera, but also extends in the same manner to other plants.

The active compound combinations to be used in accordance with the invention can be employed not only in conventional cultivation methods (suitably spaced row crops), in plantation crops (for example grapevines, fruit, citrus) and in industrial plants and railtracks, on paths and squares, but also for stubble treatment and in the minimum tillage method. They are furthermore suitable as desiccants (haulm killing in, for example, potatoes) or as defoliants (for example in cotton). They are furthermore suitable for use on non-crop areas. Other fields of application are nurseries, forests, grassland and the production of ornamentals.

The active compound combinations can be converted into the customary formulations such as solutions, emulsions, wettable powders, suspensions, powders, dusts, pastes, soluble powders, granules, suspo-emulsion concentrates, natural and synthetic materials impregnated with active compound, and microencapsulations in polymeric materials.

These formulations are produced in a known manner, for example by mixing the active compounds with extenders, that is, liquid solvents and/or solid carriers, optionally with the use of surfactants, that is, emulsifiers and/or dispersants and/or foam formers.

If the extender used is water, it is also possible to employ, for example, organic solvents as cosolvents. The following are essentially suitable as liquid solvents: aromatics such as xylene, toluene, or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water.

Solid carriers which are suitable are:

for example ammonium salts and ground natural minerals such as kaolins, clays, talc, chalk, quartz, attapulgite, montmorillonite or diatomaceous earth, and ground synthetic materials such as highly-dispersed silica, alumina and silicates; suitable solid carriers for granules are for example crushed and fractionated natural rocks such as calcite, marble, pumice, sepiolite and dolomite, or else synthetic granules of inorganic and organic meals, and granules of organic material such as sawdust, coconut shells, corn cobs and tobacco stalks; suitable emulsifiers and/or foam formers are for example nonionic and anionic emulsifiers such as polyoxyethylene fatty acid esters, polyoxyethylene fatty alcohol ethers, for example alkylaryl polyglycol ethers, alkylsulphonates, alkyl sulphates, arylsulphonates, or else protein hydrolyzates; suitable dispersants are for example ligninosulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 percent by weight of active compounds, preferably between 0.5 and 90%.

The active compound combinations according to the invention are generally applied in the form of ready mixes. However, the active compounds contained in the active compound combinations may also be applied in the form of individual formulations which are mixed upon use, that is, in the form of tank mixes.

The novel active compound combinations, as such or in their formulations, may furthermore also be used as a mixture with other known herbicides, again with ready mixes or tank mixes being possible. A mixture with other known active compounds such as fungicides, insecticides, acaricides, nematicides, bird repellents, growth substances, plant nutrients and soil conditioners is also possible. It may furthermore be advantageous for specific applications, in particular for the post-emergence method, to incorporate into the formulations plant-compatible mineral or vegetable oils (for example the commercial product "Rako Binol") or ammonium salts such as, for example, ammonium sulphate or ammonium thiocyanate, as further additives.

The novel active compound combinations can be used as such, in the form of their formulations or the use forms which can be prepared from these formulations by further dilution, such as ready-to-use solutions, suspensions, emulsions, powders, pastes and granules. Application is effected in the customary manner, for example by pouring, spraying, atomizing, dusting or broadcasting.

The active compound combinations according to the invention can be applied before and after emergence of the plants, that is to say by the pre- and post-emergence method. They may also be incorporated into the soil prior to sowing.

The good herbicidal activity of the novel active compound combinations is demonstrated by the examples below. Whereas there are deficits in the herbicidal action of the individual active compounds, the combinations all have very good action against weeds which exceeds a simple addition of activities.

A synergistic effect in herbicides is always present when the herbicidal action of the active compound combination exceeds the action of the active compounds when applied individually.

The expected action for a given combination of two herbicides can be calculated as follows (cf. COLBY, S. R.: "Calculating synergistic and antagonistic responses of herbicide combinations", Weeds 15, pages 20-22, 1967):

If $X$=% damage by herbicide A (active compound of the formula I) at an application rate of p kg/ha and $Y$=% damage by herbicide B (active compound of the formula II) at an application rate of q kg/ha and $E$=the expected damage of herbicides A and B at an application rate of p and q kg/ha, then $$E = X + Y - (X*Y/100).$$

If the actual damage exceeds the calculated value, the combination has a superadditive effect, that is to say a synergistic effect.

The expected activity for a given combination of three herbicides can likewise be found in the literature cited above.

USE EXAMPLES

The required amount of active compound—or formulation—is dissolved in 2 to 3 ml of the solvent (acetone or N,N-dimethylformamide), an emulsifier (1 ml) is added, if required, and the solution is diluted with water to the desired concentration.

Mixtures are prepared by mixing a predetermined dissolved amount of the first active compound with the required amount of the second active compound—and, if appropriate, with additional active compounds or other ingredients—and the mixture is then diluted with water to the desired concentration.

In the case of post-emergence tests, a surfactant (for example Renex 36) is usually added in a concentration of 0.1% to the spray solution.

The amount of active compound is chosen such that the desired application rate per hectare (ha) is achieved.

Example A

Post-Emergence Test (Greenhouse)

Test plants are grown under controlled conditions (temperature and light). Once the plants have reached a height of 5 to 15 cm, the test compound or combination of test compounds is sprayed such that the particular amounts of active compound desired are applied per unit area. The concentration of the spray liquor is chosen such that the particular amounts of active compound are applied in 500 litres of water per hectare.

Following the spray application, the plant containers are placed in a greenhouse under constant conditions with respect to light and temperature.

After about three weeks, the degree of damage to the plants is rated in % damage in comparison to the development of the untreated control.

The figures denote:

0%=no effect (like untreated control)

100%=total destruction

Active compounds, application rates, test plants and results are shown in the tables below, the terms used in the tables having the following meanings:

a.i.=active ingredient (active compound)

ha=hectare

In the table, metribuzin is a 70 WG formulation of the corresponding active compound ("Sencor 70 WG").

In the table, sulcotrione is a 300 SC formulation of the corresponding active compound ("Mikado 300 SC").

TABLE A1

| Active compound (formulation) | Application rate (g of ai/ha) | Chenopodium album observed | Chenopodium album calculated* |
|---|---|---|---|
| metribuzin | 10 | 0 | |
| sulcotrione | 20 | 90 | |
| metribuzin + sulcotrione | 10 + 20 | 100 | 90 |

TABLE A2

| Active compound (formulation) | Application rate (g of ai/ha) | Polygonum convolvolus observed | Polygonum convolvolus calculated* |
|---|---|---|---|
| metribuzin | 40 | 0 | |
|  | 20 | 0 | |
| sulcotrione | 80 | 60 | |
|  | 40 | 30 | |
|  | 20 | 0 | |
| metribuzin + sulcotrione | 40 + 80 | 100 | 60 |
|  | 40 + 40 | 90 | 30 |
|  | 40 + 20 | 60 | 0 |
|  | 20 + 80 | 100 | 60 |
|  | 20 + 40 | 80 | 30 |
|  | 20 + 20 | 60 | 0 |

TABLE A3

| Active compound (formulation) | Application rate (g of ai/ha) | Amaranthus retroflexus observed | Amaranthus retroflexus calculated* |
|---|---|---|---|
| metribuzin | 20 | 90 | |
|  | 10 | 80 | |

TABLE A3-continued

| Active compound (formulation) | Application rate (g of ai/ha) | Amaranthus retroflexus observed | Amaranthus retroflexus calculated* |
|---|---|---|---|
| sulcotrione | 80 | 60 | |
| | 40 | 20 | |
| metribuzin + sulcotrione | 20 + 80 | 100 | 96 |
| | 20 + 40 | 100 | 92 |
| | 10 + 80 | 100 | 92 |
| | 10 + 40 | 100 | 84 |

(500 ml/ha of Marlipal were added as additive)

TABLE A4

| Active compound (formulation) | Application rate(g of ai/ha) | Polygonum convolvolus observed | Polygonum convolvolus calculated* |
|---|---|---|---|
| metribuzin | 40 | 0 | |
| | 20 | 0 | |
| sulcotrione | 80 | 70 | |
| | 40 | 20 | |
| metribuzin + sulcotrione | 40 + 80 | 100 | 70 |
| | 40 + 40 | 70 | 20 |
| | 20 + 80 | 95 | 70 |
| | 20 + 40 | 70 | 20 |

(500 ml/ha of Marlipal were added as additive)

TABLE A5

| Active compound (formulation) | Application rate (g of ai/ha) | Echinochloacrus galli observed | Echinochloacrus galli calculated* |
|---|---|---|---|
| metribuzin | 40 | 10 | |
| | 20 | 0 | |
| | 10 | 0 | |
| sulcotrione | 80 | 80 | |
| | 40 | 40 | |
| | 20 | 20 | |
| metribuzin + sulcotrione | 40 + 80 | 100 | 82 |
| | 40 + 40 | 100 | 46 |
| | 40 + 20 | 95 | 28 |
| | 20 + 80 | 100 | 80 |
| | 20 + 40 | 90 | 40 |
| | 20 + 20 | 60 | 20 |
| | 10 + 80 | 95 | 80 |

(500 ml/ha of Marlipal were added as additive)
*The calculated values were determined using Colby's formula.

The invention claimed is:

1. A herbicidal composition comprising an effective amount of an active compound combination comprising
   (a) 4-amino-6-(1,1-dimethylethyl)-3-methylthio-1,2,4-triazin-5(4H)-one (metribuzin),
   and
   (b) 2-(2-chloro-4-methylsulphonylbenzoyl)-1,3-cyclohexanedione (sulcotrione), wherein from 0.02 to 50 parts by weight of component (b) are present per part by weight of component (a),
   and
   (c) optionally, a compound that improves crop plant compatibility selected from the compounds 1-methylhexyl 5-chloroquinoxalin-8-oxyacetate (cloquintocet-mexyl), α-(cyanomethoximino)phenylacetonitrile (cyometrinil), 2,4-dichloro-phenoxyacetic acid (2,4-D), 4,6-dichloro-2-phenylpyrimidine (fenclorim), ethyl 1-(2,4-dichlorophenyl)-5-trichloromethyl-1H-1,2,4-triazole-3-carboxylate (fenchlorazol-ethyl), phenylmethyl 2-chloro-4-trifluoromethylthiazole-5-carboxylate (flurazole), 4-chloro-N-(1,3-dioxolan-2-ylmethoxy)-α-trifluoro acetoxyphenoxime (fluxofenim), ethyl 4,5-dihydro-5,5-diphenyl-3-isoxazole-carboxylate (isoxadifen-ethyl), diethyl 1-(2,4-dichlorophenyl)-4,5-dihydro-5-methyl-1H-pyrazole-3,5-dicarboxylate (mefenpyr-diethyl), 2-dichloromethyl-2-methyl-1,3-dioxolane (MG-191), 1,8-naphthalic anhydride, α-(1,3-dioxolan-2-ylmethoximino)phenylacetonitrile (oxabetrinil), N-cyclopropyl-4-[[(2-methoxy-5-methylbenzoyl) amino]sulphonyl]benzamide N-[[(4-methoxyacetylamino)-phenyl]sulphonyl]-2-methoxybenzamide and N-[[(4-methylaminocarbonyl-amino)phenyl]sulphonyl]-2-methoxybenzamide,
   with the proviso that the sole herbicidally active ingredients of the herbicidal composition are metribuzin and sulcotrione and with the further proviso that no compound that improves crop plant compatibility other than a compound of optional component (c) can be present in the herbicidal composition.

2. A method for controlling unwanted plants comprising allowing a composition according to claim 1 to act on the unwanted plants and/or their habitat.

3. A process for preparing a herbicidal composition comprising mixing a composition according to claim 1 with one or more surfactants and/or extenders.

4. A herbicidal composition comprising a composition according to claim 1 and one or more surfactants and/or extenders.

* * * * *

UNITED STATES PATENT AND TRADEMARK OFFICE
CERTIFICATE OF CORRECTION

PATENT NO. : 7,612,017 B2  Page 1 of 1
APPLICATION NO. : 10/508503
DATED : November 3, 2009
INVENTOR(S) : Feucht et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1268 days.

Signed and Sealed this

Nineteenth Day of October, 2010

David J. Kappos
*Director of the United States Patent and Trademark Office*